(12) United States Patent
Linker et al.

(10) Patent No.: US 6,334,365 B1
(45) Date of Patent: Jan. 1, 2002

(54) TARGET DETECTION PORTAL

(75) Inventors: Kevin L. Linker, Albuquerque; Charles A. Brusseau, Tijeras, both of NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/734,622

(22) Filed: Dec. 11, 2000

(51) Int. Cl.[7] .................................................. G01N 1/00
(52) U.S. Cl. .................................. 73/864.81; 73/864.71
(58) Field of Search ........................... 73/863.31, 863.33, 73/863.83, 864.33, 864.34, 864.71, 864.81, 864.84

(56) References Cited

U.S. PATENT DOCUMENTS

| | | | |
|---|---|---|---|
| 4,045,997 A | * | 9/1977 | Showalter et al. |
| 4,202,200 A | * | 5/1980 | Elloson ........................ 73/23 |
| 4,896,547 A | * | 1/1990 | Arney et al. ............. 73/863.81 |
| 4,987,767 A | * | 1/1991 | Corrigan et al. ............ 73/23.36 |
| 5,827,118 A | * | 10/1998 | Johnson et al. .............. 454/187 |
| 5,914,268 A | * | 6/1999 | Linker et al. ................. 73/28.1 |
| 6,058,929 A | | 5/2000 | Fritz |
| 6,073,499 A | * | 6/2000 | Settles ...................... 73/864.81 |

OTHER PUBLICATIONS

ARTX Adjustable Air Saver Nozzles data sheet, Model 48009, p. 27, Not Dated.
ARTX's Static Elimination data sheets, pp. 32–33, Model 55000 Ionizing Bar, pp. 34 and 36; Model 50006 Ionizing Nozzles, p. 38, Not Dated.

* cited by examiner

Primary Examiner—Robert Raevis
(74) Attorney, Agent, or Firm—Suzanne L. K. Rountree; George H. Libman

(57) ABSTRACT

A portal apparatus for screening persons or objects for the presence of trace amounts of target substances such as explosives, narcotics, radioactive materials, and certain chemical materials. The portal apparatus can have a one-sided exhaust for an exhaust stream, an interior wall configuration with a concave-shape across a horizontal cross-section for each of two facing sides to result in improved airflow and reduced washout relative to a configuration with substantially flat parallel sides; air curtains to reduce washout; ionizing sprays to collect particles bound by static forces, as well as gas jet nozzles to dislodge particles bound by adhesion to the screened person or object. The portal apparatus can be included in a detection system with a preconcentrator and a detector.

24 Claims, 4 Drawing Sheets

TARGET DETECTION PORTAL

This invention was made with Government support under Contract DE-AC04-94AL85000 awarded by the U.S. Department of Energy. The Government has certain rights in the invention.

BACKGROUND OF THE INVENTION

This invention relates to the field of detection apparatus, particularly for controlled or dangerous substances, and more particularly to chemical and explosive detection apparatus for screening persons or objects for the presence of trace amounts of target substances.

U.S. Federal Aviation Administration safety concerns for the traveling public, combined with increased boldness of terrorists, has led to a need to screen for trace quantities of substances upon a person or object, in addition to the current use of metal detectors and x-ray systems. Trace detection systems, rather than bulk detection systems, are of increasing interest to identify individuals who recently have handled explosives materials by detecting trace amounts or even vapors from particular substances. Practical requirements of a detection system include the need to operate quickly in order to screen a high volume of people, high reliability of equipment for repeated and high-volume use, high accuracy, and a quick cleaning cycle after detection of a controlled or dangerous substance. It also is important that the system not occupy an excessive amount of physical space and that it be a self-contained unit with easy installation and easy operation.

DETECTION SYSTEMS

In the case of screening persons, a trace detection system must be relatively non-invasive, preferably involving no physical contact. A particulate collection and detection system that involves wiping or brushing a surface can improve test accuracy but can consume too much per-test time and can invade the physical privacy of the person being screened. Linker et al., U.S. Pat. No. 5,915,268 (1999), incorporated herein by reference, is an example of a vertical flow chemical detection portal. The U.S. Pat. No. 5,915,268 patent discloses a preferred design having two sides, two floor vents (effectively dividing the exhaust stream), two preconcentrators, and two detectors. The U.S. Pat. No. 5,915,268 patent teaches the use of a portal with each of the two sides having a top portion, a middle portion, and a bottom portion, where each portion is flat, and where the sides, along with a connecting transom, form a test space having a smaller cross-section at the bottom of the test space than at the top of the test space to partially maintain air flow velocities despite losses from an open entry side and exit from the test space. Air flow over an object picks up particles which are carried through either floor vent to a corresponding detector. The U.S. Pat. No. 5,915,268 patent does not teach the use of any means to increase sample particle collection, to contain collected particles, or to reduce washout (i.e., the reflection of air off an object in the test space causing air to wash out of open portal sides, thus reducing the number of particles in a collection sample).

Fritz, U.S. Pat. No. 6,058,929 (2000), is an example of an adjustable exhaust hood with an air curtain. The U.S. Pat. No. 6,058,929 patent teaches a varied exhaust airflow across an exhaust hood with an open underside and a grease filter, and an intake fan to create a partial air curtain to trap the flow of rising exhaust air, which is warm and laden with smoke and grease, within the exhaust hood. The U.S. Pat. No. 6,058,929 patent does not teach substance detection device having an air curtain for increased sample size.

Explosives chemicals commonly used by terrorists can have extremely low vapor pressure which can make explosives vapor detection difficult, especially in conjunction with a short screening time. Explosives detection is performed mainly by bomb-sniffing dogs, which can be time-consuming and can be physically intrusive and intimidating to people. Detection systems can use highly sensitive detectors in order to detect trace amounts of explosives chemicals. A collection system that does not account for sample losses due to washout can be limited in its probability of detection of trace amounts of explosives and controlled substances. An improved collection system, which does not lose a significant portion of a collection sample due to washout and which can concentrate the collection sample prior to detection analysis, can increase the probability of detection.

There is a need for a non-invasive, privacy-protecting, detection portal comprising a collection system that is capable of containing a collection sample of trace amounts of a substance, limiting sample losses due to washout, and collecting a larger number of sample particles in order to effectively increase the probability of detection.

SUMMARY OF THE INVENTION

This invention provides a portal apparatus suitable for screening a person or other object for the presence of trace amounts of a target substance substantially thereon. The portal apparatus comprises a portal comprising two facing sides and a transom, together forming a test space, where the two facing sides comprise substantially vertical walls, configured in a concave shape across a horizontal cross-section for reducing washout from an open entry side and/or an open exit side. The portal apparatus comprises a plurality of gas nozzles for dislodging particles of the target substance on the object and a plurality of ionizing spray devices for dislodging particles of the target substance by ionization. The portal apparatus further comprises an air curtain. In a preferred embodiment, the portal apparatus further consists of one-sided exhaust through a floor vent intake.

This invention provides a detection system suitable for screening a person or other object for the presence of trace amounts of a target substance substantially thereon. The detection system comprises a portal, a preconcentrator, a detector, and a collector subsystem comprising: an airflow device, gas nozzles for dislodging particles of the target substance on the object, and ionizing spray devices for dislodging particles by ionization. The portal can comprise two facing sides, where each side is substantially concave-shaped across a horizontal cross-section. In a preferred embodiment, the portal apparatus further consists of one-sided exhaust through a floor vent intake.

BRIEF DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

Figure 1:
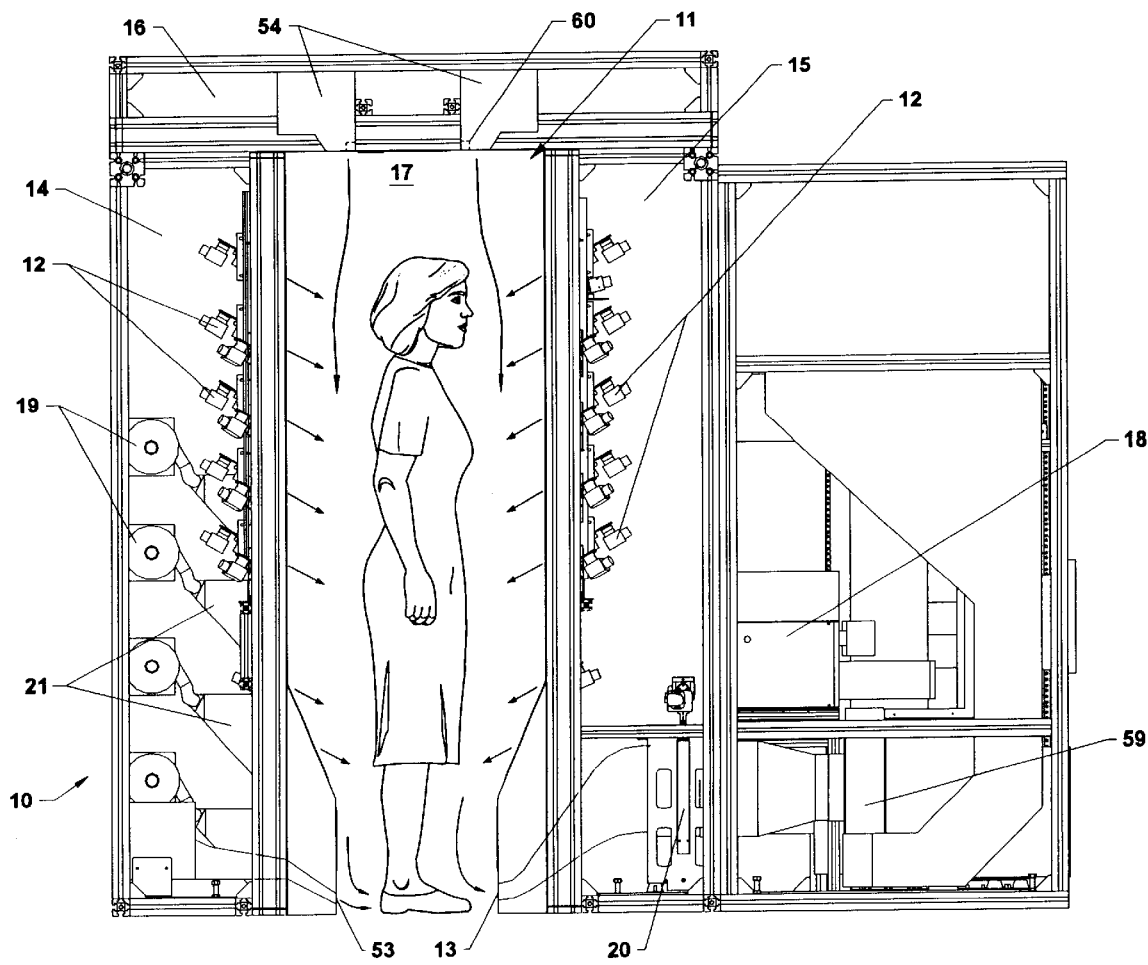
FIG. 1 is an front entry view of an embodiment of the present invention, with a portion broken away to show certain interior elements.

This invention provides a portal apparatus suitable for screening a person or an object for the presence of trace amounts of a target substance substantially thereon. The present invention provides a detection system suitable for screening a person or an object for the presence of trace amounts of a target substance substantially thereon. Examples of target substances requiring detection and screening include but are not limited to: trace amounts of explosives, bulk explosives, narcotics, chemical materials, radioactive materials, particles, vapors, and various combinations.

Embodiments of the apparatus can be adapted to collect and detect more than one target substance in a single pass through the apparatus.

Various embodiments, comprising different combinations of novel features, can be advantageous in different applications using the invention. For example, a target detection portal can be used at airport terminals for screening airline passengers; at facilities handling nuclear materials for screening exiting personnel; at border-crossings in screening for narcotics and controlled substances; and at prisons, schools, courthouses, entertainment facilities, or any public facilities, in screening for illegal or controlled substances.

TERMINOLOGY

An "object" to be screened includes people and animals, for example, as well as inanimate objects such as packages and luggage. A very large detector can be used to screen vehicles at border crossings.

A "target substance" can mean any substance to be screened by detection of particles on objects, and can include, but is not limited to, narcotics, bulk explosives, trace explosives, controlled substances, illegal drugs and chemicals, nuclear material, constituents and by-products of the above, and combinations thereof.

A "particle" can be particulate matter of substantially any size, and includes but is not limited to droplets, vapors, large molecules, and solid particles. There can be zero particles of the target substance detected.

In this specification, "back" and "front" in reference to the figures corresponds to directions "into" and "out of" the plane of the drawing paper, respectively. "Right" and "left" sides in the figures correspond to the right and left directions while viewing the figures with the "front" coming "out of" the plane of the drawing paper, according to a conventional meaning. In addition, the "front" of a detection portal is referred to as the "front entry side" with "entry" edges and "entry" horizontal air curtains, while the "back" of the detection portal is referred to as the "rear exit side" with "exit" edges and "exit" horizontal air curtains.

While air is the preferred embodiment, a flow over the object can be any gas.

DETECTION PORTAL

Figure 3:
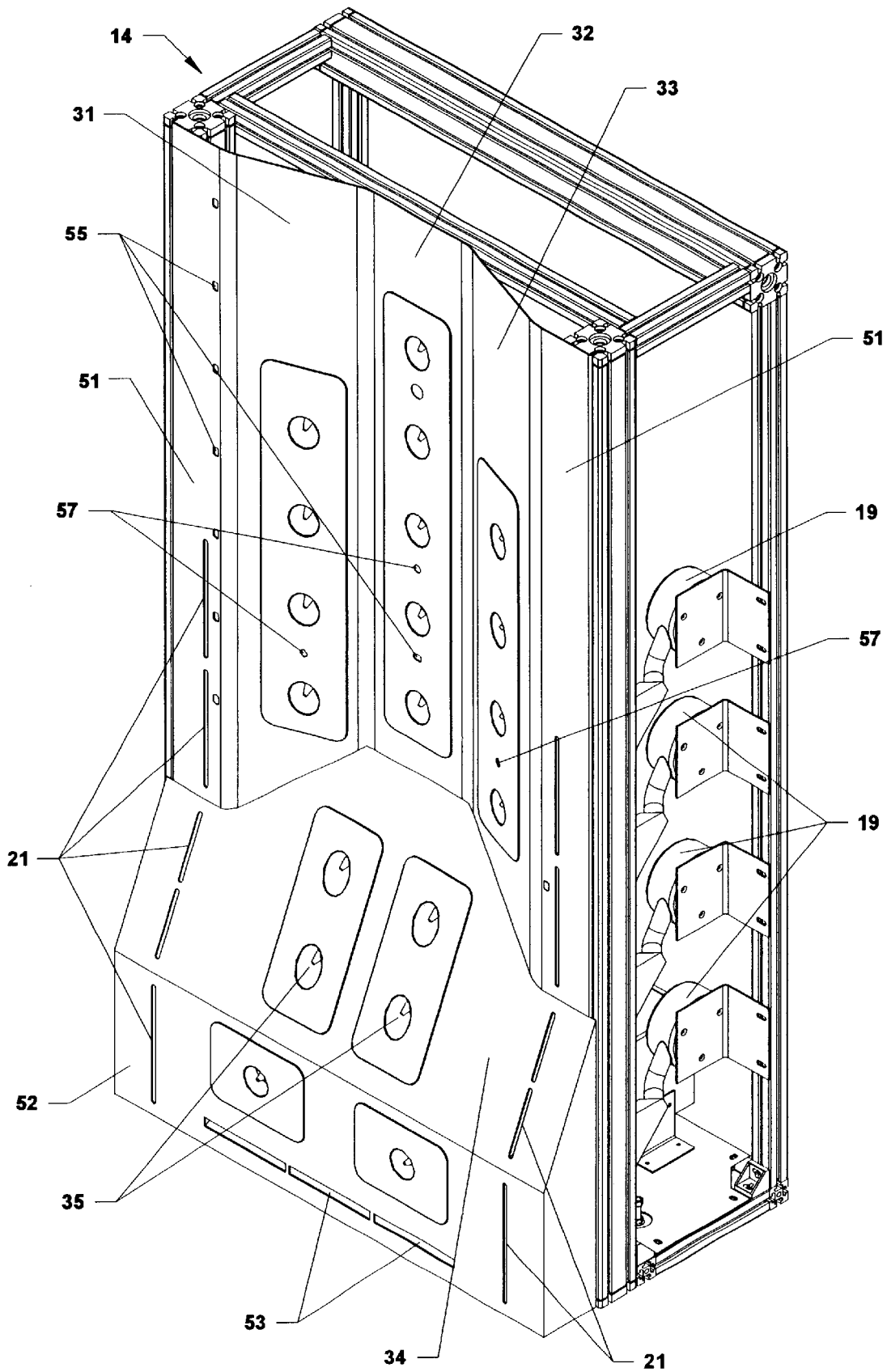
FIG. 3 is a detailed view of an embodiment of the present invention, showing details of a side as partially visible in FIG. 2.
Figure 4:
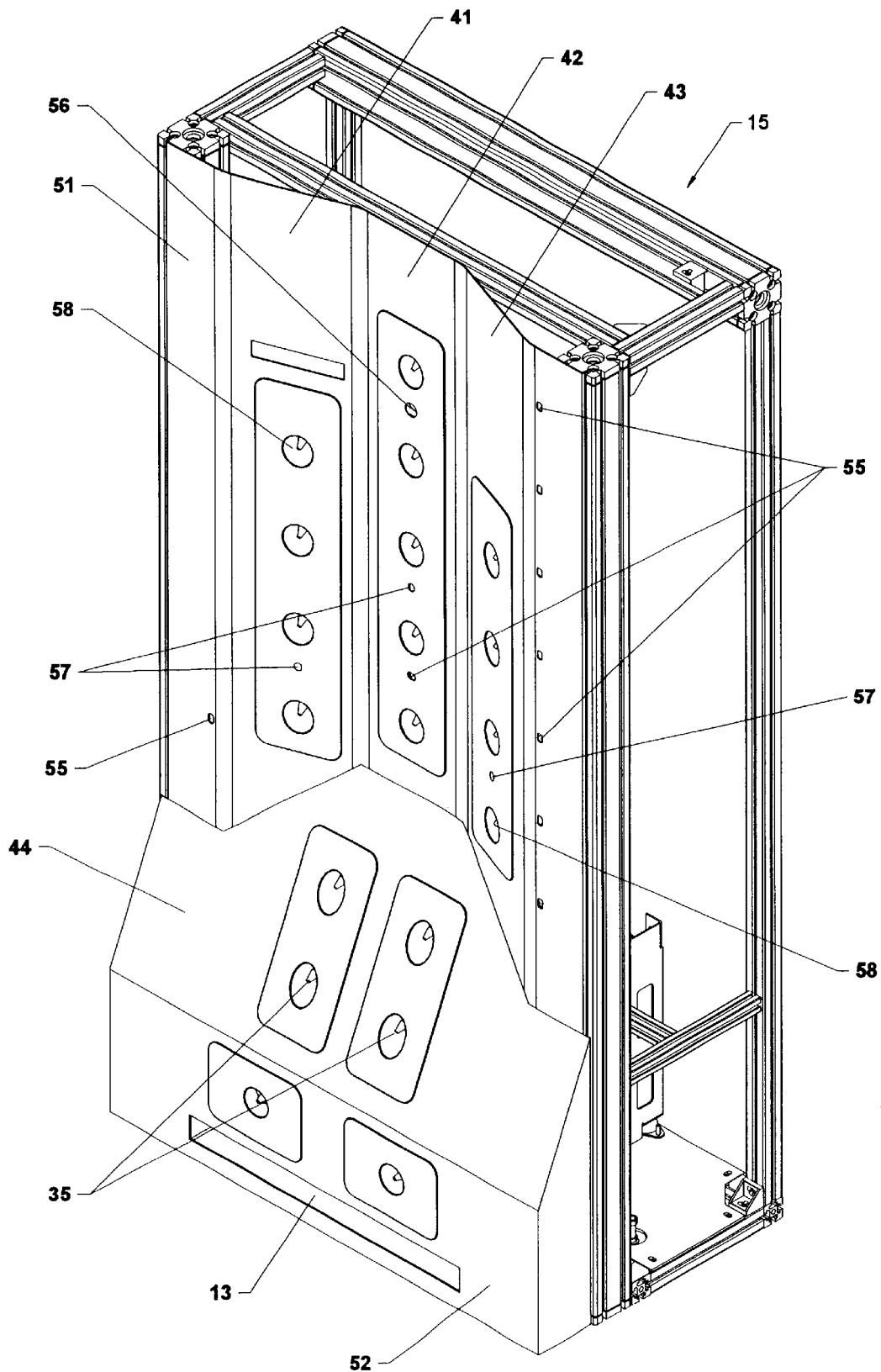
FIG. 4 is a detailed view of an embodiment of the present invention, showing details of a side as obscured in FIG. 2.

FIG. 1 is a front entry view of an embodiment of the present invention, with a portion broken away to show certain interior elements. In this embodiment, target detection portal 10, as shown in FIG. 1, is a portal apparatus comprising portal 11, nozzle valves 12, and floor vent intake 13. Portal 11 in this embodiment comprises two facing sides 14, 15 and transom 16 extending between the respective tops of sides 14, 15. The space beneath transom 16 and between sides 14, 15, extending from a bottom to a top, comprises test space 17. As in the '268 patent, air stream flow is from top to bottom of test space 17 within portal 11, where one or more fans 54 mounted with transom 16 initiate the airflow by pulling ambient air into portal 11. Fan 54 is not required to start the airflow. Fan 54 can include vertical air generators and vertical air curtains and can be combined with ionizing devices such as ionizing bars 60. It is desirable to create an air stream flow of approximately 400 fpm from top to bottom. Fan 59, shown in FIG. 1, is used to create negative pressure (for example; a pressure drop between test space 17 and fan 59) to draw the air stream flow from portal 11 and to exhaust air from portal 11 through floor vent intake 13. As shown in FIGS. 3 and 4, each side 14, 15 can comprise a plurality of substantially vertical inside walls, configured in a substantially concave shape across a horizontal cross-section of each respective side 14, 15.

Nozzle valves 12 can be mounted with sides 14, 15 and direct a gas stream into test space 17. Additional nozzle valves 12 and one or more fans 54 can be mounted with transom 16 and direct the gas stream downward. In the embodiment shown in FIG. 1, floor vent intake 13 is mounted with the bottom of side 15, at a cross section appropriate to provide a vent face velocity of approximately 2000 fpm. Near the floor, target detection portal 10 can be viewed as an open vapor tank with exhaust vapor coming off the surface. To achieve constant airflow across the floor (for example, a velocity of 2000 fpm) and to provide a particle capture region near a person's feet, the length and height of floor vent intake 13 can be determined using equations for open vapor tanks. Since particles can adhere to shoes due to contact with the ground, a lower-body-level capture region can-collect those particles.

In operation, the gas stream from nozzle valves 12 moves downwardly over the object in test space 17 and exhausts through floor vent intake 13, through vents to preconcentrator 20 and detector 18. This invention embodiment consists of a one-sided exhaust through floor vent intake 13 and has supply vent 53 mounted with opposing side 14, as shown in FIG. 1. Unlike the two-sided exhaust of the '268 patent, this one-sided exhaust concentrates the exhaust stream and directs the entire stream through floor vent intake 13 to one detector. Supply vent 53, in a preferred embodiment, is a supply fan at foot-level to move air from the object's back to front and toward floor vent intake 13, effectively providing zone capture in front of floor vent intake 13. Several benefits accrue in such a system: lower cost for only one vent structure, one preconcentrator, and one detector, a concentrated gas exhaust stream not diluting the test sample between two or more exhaust streams; improved collection near floor-level with supply vent 53 and floor vent intake 13; and smaller floor space requirement for the apparatus. In a preferred embodiment, preconcentrator 20 is a two-stage device for concentrating a sample prior to passing it through detector 18. See Linker, et al., U.S. patent application Ser. No. 09/594,215, incorporated herein by reference.

Another embodiment uses vertical and horizontal air curtain generators. This embodiment can utilize horizontal air curtains extending from an edge of side 14 to side 15, shown in FIGS. 1 and 2. As also shown in FIG. 3, air curtain blowers 19 move air through air curtain ports 21 mounted with side 14 and across each opening (i.e., front entry side and rear exit side) of portal 11 to create horizontal air curtains moving from side 14 to side 15). The horizontal air curtains reduce washout from portal 11 of an air stream containing a test sample. Air curtain blowers 19 and air curtain ports 21 can be installed from floor level up to a desired height fine-tuned to maximize washout reduction while minimizing the number of air curtain blowers and the introduction of additional air into the system (for example, approximately 4 feet high on a portal sized for a standing adult). Air curtain blowers 19 can inject a high velocity (for example, 500 to 1000 fpm) and low volume (for example, from 5 to 10 cfm) air flow from back to front. The horizontal air curtain can comprise multiple air curtain blowers 19 and air curtain ports 21 to fine-tune a curtain height to reduce washout and air stream flow from portal 11. Air curtain blowers 19 are preferably oriented inward from a vertical plane and toward test space 17 and inclined downward from a horizontal plane to further reduce washout. Tests on a mock-up portal with fog injected into a flow stream showed fog washing out of the portal without an air curtain and showed reduced washout with the air curtain extending up to 12 inches in height. An embodiment using air curtains can comprise an entry air curtain and an exit air curtain, with air curtain blowers 19 and air curtain ports 21 mounted on a front edge of side 14 and a rear edge of side of side 14, respectively. In an embodiment with air curtains, the air curtains should add only enough air volume to reduce washout without significantly increasing the amount of air to be exhausted from the portal.

Several benefits can accrue in an embodiment with air curtains: reduced portal washout, increased number of particles in the test sample due to containment, higher probability of detection of the target substance, and potential lower cost for a less sensitive detector due to increased test sample size. An example suitable air curtain includes Lead Edge's ventilation products model C2400-1115F, which was used in a prototype device. Other commercial high-pressure blowers and ducts also can be used.

An embodiment with nozzle valves 12 can comprise gas jet nozzles 58 and ionizing air spray devices 57. Particles bound to the object by mechanical adhesion forces can be removed by nozzles 58 that emit a high velocity gas jet that overcome each particles' adhesion force. An example of such gas nozzles includes but is not limited to: Model 48009 adjustable air saver nozzles manufactured by ARTX (The Air Research Technology Company) in Cleveland, Ohio. See ARTX Adjustable Air Saver Nozzles data sheet, Model 48009, page 27, incorporated herein by reference. ARTX saver nozzles provide high thrust with very low compressed air consumption and can operate with a small amount of compressed air at near-sonic velocity exiting through a narrow slot around a nozzle base. As the high-speed "tube" of air emerges from the slot and travels down a cone-shaped nozzle, it creates a strong vacuum along the surface entraining a much larger volume of surrounding into the airstream. The ARTX saver nozzle can multiply input air by a factor of 25 to 1. Gas saver nozzles dislodge particulate bound by mechanical adhesion from an object without the addition of substantial amounts of gas to be exhausted from the portal.

Ionizing spray devices 57 can be used to remove particulate bound to a surface by static electricity by deionizing or neutralizing the static forces. Ionizing air spray devices can be especially effective with chemical particulate, such as explosive residue, which can be attached to a surface by both adhesion and static forces. A preferred embodiment comprises at least two ionizing spray devices. Each ionizing spray device, as currently manufactured, can be effective for approximately 1 to 2 seconds, then the air recombines with the ions. Tests have shown that it takes approximately 2 seconds for particles to reach the floor from the top of the portal. Examples of ionizing spray devices can include: ionizing air jets, ionizing nozzles, ionizing bars 60, electrically neutral air spray emitters, static force neutralizers, and combinations of the above. One prototype embodiment of the present invention combined commercially available ionizing bar (model 55000 available from ARTX) with an overhead fan and ionizing nozzles (model 50006 available from ARTX). See ARTX's Static Elimination data sheets, pages 32–33; Model 55000 Ionizing Bar, pages 34 and 36; Model 50006 Ionizing Nozzles, page 38; incorporated herein by reference. ARTX's ionizing nozzles operate by emitting a low velocity, electrically neutral air spray over a large area. As the electrically neutral air contacts a statically-bound particle, the particle and surface it is attached to are no longer electrically opposite. The particle can be released from the surface and can be removed by the high velocity jet nozzles described above.

Figure 2:
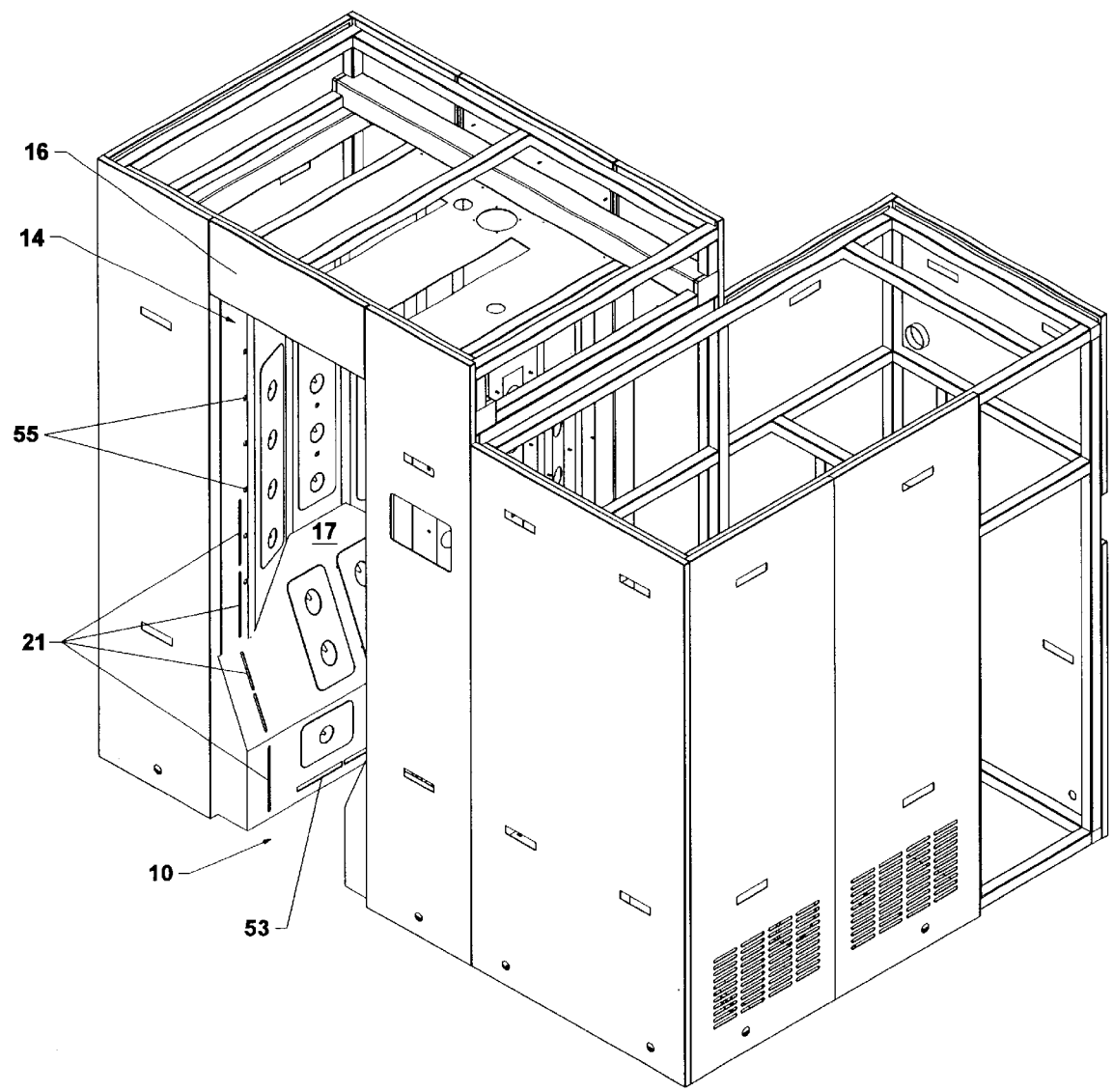
FIG. 2 is a partially exploded perspective view, from above, of an embodiment of the present invention.

FIG. 2 is a partially exploded perspective view, from above, of an embodiment of the invention. Test space 17 has an entry toward the front of the drawing page and an exit toward the back of the drawing page. The one-sided exhaust, floor vent intake 13, is hidden on the right side of target detection portal 10.

Another embodiment of the present invention can comprise activator 55 mounted with sides 14, 15. Activator 55 can serve two purposes: to detect an object within test space 17 and to sequentially initiate nozzle valves 12 from a top to a bottom of portal 11. Nozzle valves 12 can be timed to also initiate from top to bottom and can reinforce airflow initiated by transom fans 54 (shown in FIG. 1). Activator 55 can measure a height of the object within test space 17 and can initiate nozzle valves 12 according to an activation criterion. In one embodiment, activator 55 can comprise vertically-arranged photocells with opposing light sources (for example, receivers and emitters), mounted with sides 14, 15 to measure the height of the object being screened and to turn on nozzles according to an activation criterion. Example activation criteria, which serve to illustrate but to not limit, include: only activating nozzles below the height of the object, only activating nozzles a certain distance below a person's height so as to avoid firing a high-velocity gas jet toward the person's face; activating all ionizing air spray devices upon entry of an object and sequentially activating gas jet nozzles mounted below the object's height; and other activation sequences that can be initiated by activator 55. Examples of activator 55 include: photocells, infrared detectors, light bars, timers, on-off devices, and any combinations of the above. One prototype device used an infrared photocell for activator 55. Camera 56 also can be used in the device.

FIGS. 3 and 4 are detailed views of an embodiment of the present invention showing details of the sides of the structure shown in FIG. 2. Side 14 in FIG. 3 corresponds to the "left" side of the portal apparatus embodiment shown in FIGS. 1 and 2. As seen in FIG. 3, side 14 can comprise a plurality of substantially vertical inside walls 31, 32, 33, configured in the substantially concave shape across a horizontal cross-section of side 14.

Side 14 can comprise inside walls 31, 33 canted inward about 20 degrees toward test space 17, and inside wall 32 set back about 4 inches from an edge of side 14 resulting in a substantially concave shape across a horizontal cross-section of side 14. In such an embodiment, with side 15 configured similarly to side 14, the object being screened is in a more cylindrically shaped test space 17 that can allow for better airflow and directioning of nozzle valves 12 than would equivalent planar walls. More wall surfaces with more orientations can be available for nozzle placement. In a portal design with planar walls, when the nozzles fire there can be significant reflection of air off the object being screened causing air to wash out of the portal. Concave interior walls across a horizontal cross-section of sides 14, 15, as taught in this embodiment, can focus nozzle valves 12 inward and can reduce the amount of reflection and the amount of air washout from portal 11.

In an embodiment with sloped wall 34, sloped wall 34 can be below and connected to inside walls 31, 32, 33. Nozzle valves 12 can comprise lower nozzles 35 mounted within slots in sloped wall 34 and directing gas stream into test space 17. Lower nozzles 35 can direct gas or air toward a lower portion of the object, such as a person's legs, for increased test sample collection.

FIG. 4 is a detailed view of an embodiment of the present invention, showing details of a side as obscured in FIG. 2. Side 15 in FIG. 4 corresponds to the "right" side of the portal apparatus embodiment shown in FIGS. 1 and 2. As seen in FIG. 4, side 15 can comprise a plurality of substantially vertical inside walls 41, 42, 43, configured in the substantially concave shape across the horizontal cross-section of side 15.

Side 15 can comprise inside walls 41, 43 canted inward about 20 degrees toward test space 17, and inside wall 42 set back about 4 inches from an edge of side 15 resulting in a substantially concave shape across a horizontal cross-section of side 15. In such an embodiment, with side 14 configured similarly to side 15, the object being screened is in a more cylindrically shaped test space 17 that can allow for better airflow and directioning of nozzle valves 12. More wall surfaces with more orientations can be available for nozzle placement.

In an embodiment with sloped wall 44, sloped wall 44 can be below and connected to inside walls 41, 42, 43. Nozzle valves 12 can comprise lower nozzles 35 mounted within slots in sloped wall 44 and directing gas stream into test space 17. Lower nozzles 35 can direct gas or air toward a lower portion of the object, such as a person's legs, for increased test sample collection.

In an embodiment with border wall 51, border wall 51 can be beside and connected to inside wall 31 and/or inside wall 33 and/or inside wall 41 and/or inside wall 43. In an embodiment with bottom wall 52, bottom wall can be below and connected to sloped wall 34 and/or sloped wall 44. Sloped walls 34, 44 can reduce the amount of air that needs to be moved at the bottom of portal 11. Also, with a smaller horizontal cross-section, the capture zone in front of floor vent intake 13 requires less air movement generated from supply vent 53 at the heels of the object being screened.

Although the present invention has been described in detail with respect to particular embodiments, other embodiments can achieve the same results. For example, instead of two openings of portal 11 (i.e., front entry side and rear exit side), one opening can be closed (e.g., a wall can extend from one entry edge to the other entry edge) and portal 11 can have only one opening that serves as both an entry and an exit. The single-opening type of apparatus can be used whenever pass-through capabilities are not required. Another variation, similar in appearance to a Mardex booth, for example, could have one or two doors instead of air curtains to contain particles and reduce washout. Other variations and modifications of the present invention will be obvious to those skilled in the art.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A portal apparatus for screening an object for the presence of a target substance substantially thereon, the portal apparatus comprising:
   a) a portal comprising:
      i) two facing sides, each side extending from a bottom to a top, and from an entry edge to an exit edge;
      ii) a transom extending between the respective tops of the two facing sides, wherein the space beneath the transom and between the two facing sides comprises a test space for the object;
      iii) wherein each of said sides is configured in a substantially concave shape across a horizontal cross-section of each side;
   b) a plurality of nozzles, mounted with each of the two facing sides, for directing a gas stream into the test space; and
   c) a floor vent intake near the bottom in only one of s aid sides, wherein a negative pressure is utilized to draw a test sample carried by the gas stream in the test space through the floor vent intake to a detector.

2. The portal apparatus of claim 1, wherein each of said sides comprises a plurality of substantially vertical inside walls.

3. The portal apparatus of claim 2,
   a) wherein each of said two facing sides further comprises a sloped wall below and connected to the plurality of substantially vertical inside walls; and
   b) wherein the plurality of nozzles comprises a plurality of lower nozzles mounted with the sloped wall.

4. The portal apparatus of claim 1, further comprising a supply vent in one of said sides opposite the floor vent intake, wherein air from the supply vent is directed towards the floor vent.

5. The portal apparatus of claim 1, further comprising a horizontal air curtain generator mounted with said sides, and generating an air curtain extending from an edge of one side to the other side.

6. The portal apparatus of claim 5, wherein the air curtain generator comprises an entry edge air curtain generator and an exit edge air curtain generator.

7. The portal apparatus of claim 5, wherein the air curtain is oriented toward the test space, and wherein the air curtain is inclined downward from horizontal.

8. The portal apparatus of claim 1, further comprising a vertical air generator, mounted with the transom, moving air down through the test space.

9. The portal apparatus of claim 1, wherein the plurality of nozzles comprises:
   a) a plurality of gas jet nozzles; and
   b) a plurality of ionizing spray devices.

10. The portal apparatus of claim 9, wherein the plurality of ionizing spray devices is selected from the group consisting of: ionizing air jets, ionizing nozzles, ionizing bars, electrically neutral spray emitters, static force neutralizers, and combinations thereof.

11. The portal apparatus of claim 1, further comprising an activator, mounted with said sides, detecting the object in the test space and sequentially initiating each nozzle in the plurality of nozzles.

12. The portal apparatus of claim 11, wherein the activator is selected from the group consisting of: photocells, infrared detectors, light bars, and combinations thereof.

13. The portal apparatus of claim 1, further comprising an activator, mounted with said sides, measuring a height of the object and initiating one or more nozzles in the plurality of nozzles according to an activation criterion.

14. The portal apparatus of claim 1, wherein the target substance is selected from the group consisting of: trace-explosives, bulk explosives, narcotics, chemical materials, radioactive materials, particles, vapors, and combinations thereof.

15. A detection system for screening an object for the presence of a target substance substantially thereon, the detection system comprising:
   a) a portal;
   b) a collector subsystem, mounted with the portal, the collector subsystem comprising:
      i) a plurality of ionizing spray devices for deionizing particles of the target substance;
      ii) a plurality of gas jet nozzles for dislodging particles of the target substance;
      iii) an airflow device, generating an airflow within the portal for carrying the particles of the target substance; and
      iv) a floor vent intake, mounted with the portal, and having a negative pressure applied thereto, wherein the particles of the target substance carried by the airflow exit the collector subsystem;
   c) a detector, accepting the airflow from the floor vent intake, and analyzing the particles of the target substance carried by the airflow.

16. The detection system of claim 15, consisting of one exhaust through the floor vent intake.

17. The detection system of claim 15, further comprising a supply vent, mounted with the portal opposite the floor vent intake.

18. The detection system of claim 15, wherein the portal comprises two facing sides, wherein each side is substantially concave-shaped across a horizontal cross-section of each side.

19. The detection system of claim 15, wherein the collector subsystem further comprises an air curtain generator mounted with the portal.

20. The detection system of claim 15, further comprising an activator, mounted with the portal, sequentially initiating each nozzle in the plurality of gas jet nozzles from a top to a bottom of the portal.

21. The detection system of claim 15, further comprising an activator, mounted with the portal, measuring a height of the object and initiating one or more nozzles in the plurality of gas jet nozzles according to an activation criterion.

22. The detection system of claim 15, wherein the detector is selected from the group consisting of: mass spectrometers, ion mobility spectrometers, gas chromatographs, electron capture detectors, chemiluminescence devices, time-of-flight measurers, radioactivity detectors, and combinations thereof.

23. The detection system of claim 15, wherein the collector subsystem further consists of one preconcentrator, accepting the airflow from the floor vent intake and directing the sample to the detector.

24. A portal apparatus for screening an object for the presence of a target substance substantially thereon, the portal apparatus comprising:
   a) a portal comprising:
      i) two facing sides, each side extending from a bottom to a top;
      ii) a transom extending between the respective tops of the two facing sides, wherein the space beneath the transom and between the two facing sides comprises a test space for the object;
      iii) wherein each of the two facing sides comprises:
         (1) a plurality of substantially vertical inside walls, configured in a substantially concave shape across a horizontal cross-section of each side;
         (2) a border wall beside and connected to the plurality of substantially vertical inside walls;
         (3) a sloped wall below and connected to the plurality of substantially vertical inside walls and the border wall; and
         (4) a substantially vertical bottom wall below and connected to the sloped wall;
   b) a horizontal air curtain generator mounted with the two facing sides, generating an air curtain from an edge of one side to the other side;
   c) a vertical air generator, mounted with the transom, moving air down through the test space;
   d) a plurality of nozzles, mounted with each of the two facing sides and the transom, for directing a gas stream into the test space, the plurality of nozzles comprising:
      i) a plurality of gas jet nozzles; and
      ii) a plurality of ionizing spray devices;
   e) an activator, mounted with the two facing sides, measuring a height of the object and sequentially initiating one or more nozzles in the plurality of nozzles from a top to a bottom of the portal according to an activation criterion;
   f) a supply vent in the bottom wall; and
   g) one-sided exhaust through a floor vent intake in the bottom wall opposite the supply vent, wherein a test sample carried by the gas stream in the test space moves through the floor vent intake to a detector.

* * * * *